United States Patent [19]

Kaneko et al.

[11] Patent Number: 4,547,524

[45] Date of Patent: Oct. 15, 1985

[54] INSECTICIDAL BENZOYL HYDRAZONE DERIVATIVES

[75] Inventors: Kimiyoshi Kaneko, Isehara; Hiromichi Ishikawa, Atsugi; Satoru Moriyama, Hatano; Tsugio Uchiyama, Atsugi, all of Japan

[73] Assignee: Hokko Chemical Industry Co., Ltd., Japan

[21] Appl. No.: 466,101

[22] Filed: Feb. 14, 1983

[30] Foreign Application Priority Data

Aug. 14, 1981 [JP] Japan .................... 56-126590

[51] Int. Cl.⁴ ............... C07C 109/10; C07C 127/22; A01N 47/28; A01N 37/18
[52] U.S. Cl. ........................... 514/594; 514/615; 560/24; 560/29; 560/30; 560/34; 564/44; 564/149; 564/150
[58] Field of Search ............ 564/44, 149, 150; 560/24, 29, 30, 34; 424/322, 324; 514/594, 615

[56] References Cited

U.S. PATENT DOCUMENTS

| | | | |
|---|---|---|---|
| 3,549,572 | 12/1970 | Minagawa et al. | 564/149 X |
| 3,558,435 | 1/1971 | Rey et al. | 564/149 X |
| 3,836,580 | 9/1974 | Bruce | 564/149 |
| 3,886,211 | 5/1975 | Keenan | 564/149 X |
| 4,166,129 | 8/1979 | Aoki et al. | 564/149 X |
| 4,275,078 | 6/1981 | Aoki et al. | 564/149 X |
| 4,277,500 | 7/1981 | Rusay | 564/149 X |

FOREIGN PATENT DOCUMENTS 1085028  1/1955  France ........................ 564/149

OTHER PUBLICATIONS

Offe et al., Z. Naturfursch, vol. 78, pp. 446–462 (1952).
J. Pharm. Soc., Japan 79, 103–104 (1959).

Primary Examiner—Thomas A. Waltz
Attorney, Agent, or Firm—Abelman, Frayne, Rexac & Schwab

[57] ABSTRACT

Compounds of the formula

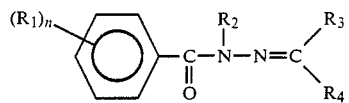

wherein $R_1$, $R_2$, $R_3$ and $R_4$ are as herein defined useful as insecticides, is described.

2 Claims, No Drawings

INSECTICIDAL BENZOYL HYDRAZONE DERIVATIVES

The present invention relates to a new class of benzoyl hydrazone derivatives and insecticides containing same. More particularly, the invention relates to a benzoyl hydrazone derivative of the general formula [I]

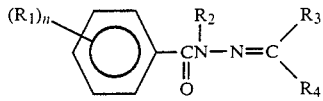

and an insecticide containing as its active ingredient said benzoyl hydrazone derivative.

Recently, a wide variety of synthetic chemicals including organo-phosphorus compounds, carbamates, synthetic pyrethroids, etc. have been developed as agents for controlling various noxions insects including those populating in farm and land (cultivated or non-cultivated) and forestry as well as in residential areas.

We synthesized a group of benzoyl hydrazone derivatives and with investigating their insecticidal activity. As its result, we have found that the benzoyl hydrazone derivatives of the general formula [I] have strong insecticidal activity against various insects as referred to above and they are surprisingly effective even against the insects of organo-phosphorus-susceptible strains. Furthermore, the benzoyl hydrazone derivatives are advantageous in their extremely low toxicity against mammels and fish.

The compounds of the invention are useful to control a variety of insects, specifically including mosquitos (*Culex pipiens pallens*, *Culex pipiens molestus*, *Aedes aegypti*, *Aedes togoi*, *Anopheles sinensis*, etc), house fly (*Musca domestica*), flesh flies, rice crane fly (*Tipula aino*), rice midge (*Chironomus oryzae*), soybean pod gall midge (*Asphondylia* sp.), oriental fruit fly (*Dacus dorsalis*), melon fly (*Dacus cucurbitae*), rice leafminer (*Hydrellia griscola*), rice whorl maggot (*Hydrellia sasakii*), rice stem maggot (*Chlorops oryzae*), stone leek leafminer (*Liriomyza chinensis*), onion maggot (*Hylemya antiqua*), secdcorn maggot (*Hylemya platura*), and so on.

Prior to the present invention there are known some compounds which are resembling to the compounds of the present invention. Such known compounds can be defined in reference to the general formula [I] wherein n is zero, $R_2$ is acetyl, benzoyl, p-nitrobenzoyl or phenyl, and both of $R_3$ and $R_4$ are methyl, and they are described in J. Pharm. Soc., Japan 79, 103–104 (1959). However, the prior art literature does disclose merely the process for the production of the compounds, which were found insecticidally weak against mosquitoes and flies. The compounds of the present invention are those obtained first by introducing a particular substituent $(R_1)_n$ into the benzoyl portion of the above-referred prior art compounds, thereby to impart surprisingly high insecticidal activity to the parent non-substituted benzoyl compounds.

The compounds of this invention can be prepared in good yield according to any of the following reaction schemes (a), (b) and (c).

Reaction scheme (a):

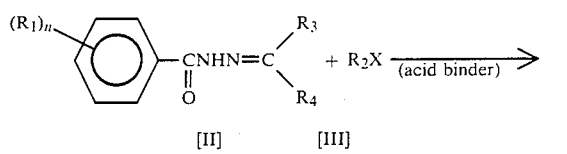

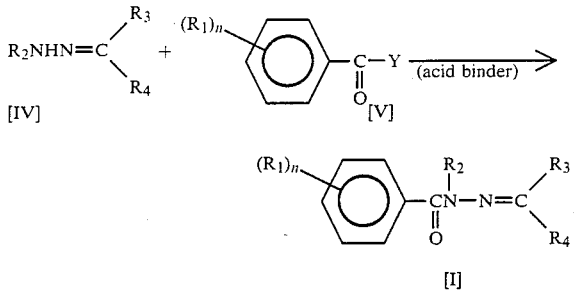

Reaction scheme (b):

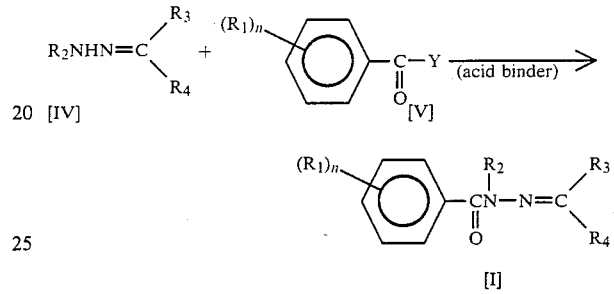

in which $R_1$, n, $R_2$, $R_3$ and $R_4$ individually have the same meanings as defined hereinbefore; X is a halogen atom, an alkylsurfuric acid residue or an arylsulfonic acid residue; and Y is a halogen atom. Accordingly, the compounds of the formula [III] can be alkyl halides, acyl halides, dialkylsurfuric acid and arylsulfonic acid esters, which are readily obtainable by the processes which per se have been known in the art. The compounds of the formula [V] are substituted benzoyl halides.

The compounds of the formula [II] are readily obtainable from a nucleically substituted benzoyl hydrazine and an aldehyde or ketone having $R_3$ and $R_4$ substituents by hydrazonation in the manner known per se. The compounds of the formula [IV] are also readily obtainable by hydrazonating the hydrazine substituted with $R_2$ in the same way.

In case of reacting a compound of the formula [II] with a compound of the formula [III] according to the reaction scheme (a) or in case of reacting a compound of the formula [IV] with a compound of the formula [V], a solvent may not be used though it is usually preferable to use an organic solvent. It is also preferable to use the compound of the formula [III] or formula [V] itself as the solvent as the case may be. Suitable solvents to be used include, for instance, hydrocarbons, halogen-substituted hydrocarbons, ethers, esters, ketones, acid amides, alcohols and dimethylsulfoxides. As acid binders, organic amines such as triethylamine and pyridine, or inorganic acid salts such as potassium carbonate are usable.

The reaction can be carried out at room temperature. However, it is preferable to use heating usually. After the reaction has completed, the acid binder salt which separates from the reaction mixture is filtered off and the filtrate is distilled to remove the solvent thereby to obtain the compound of the invention. The compound of the invention are also obtainable by adding an organic solvent such as benzene, chloroform, ether or tetrahydrofuran and water to the reaction mixture, re- This invention also provides processes for preparing the compounds of formula I or acid addition salts thereof.

Accordingly a first process for preparing compounds of formula I comprises dehydrating a compound of formula

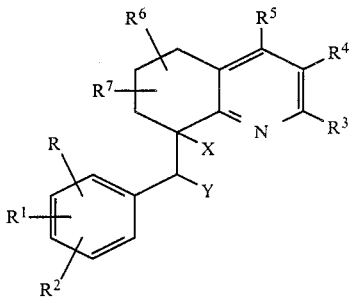
(II)

wherein one of X and Y is hydroxy, the remaining one of X and Y being hydrogen; R, $R^1$, $R^2$, $R^3$, $R^4$, $R^5$, $R^6$ and $R^7$ are as defined above, R, $R^1$ and $R^2$ each also represent hydroxy groups protected by a protecting group and removing any protecting group.

The dehydration may be carried out with usual dehydrating agents, e.g. polyphosphoric acid or with an organic acid anhydride, e.g. acetic anhydride, (in which case an acetylated derivative may be formed, from which acetic acid is eliminated to give the compound of formula I). Use of an acid anhydride to effect dehydration may also acylate any R, $R^1$ or $R^2$ hydroxy groups in which case hydrolysis may be used if desired as an after process to revert to hydroxy substituents. Also if desired any hydroxy substituents in the compound of formula II may be protected by any group known in the art for protecting hydroxy groups and then removing such protecting groups.

In this connection attention is directed to well known textbooks on peptide chemistry which illustrate such hydroxy protecting groups and methods for their removal—see for example E. Schroder and K. Lubke, "The Peptides", Volume 1, Academic Press, New York and London, 1965.

The compounds of formula II wherein X is H and Y is OH may be prepared by treatment of a compound of formula III

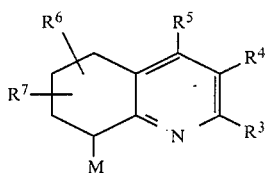
(III)

wherein $R^3$, $R^4$, $R^5$, $R^6$ and $R^7$ are as defined in connection with formula I, and M is hydrogen, an alkali metal (e.g. sodium, potassium or lithium) or MgHal, where Hal is chlorine, bromine or iodine, with an aldehyde of formula IV

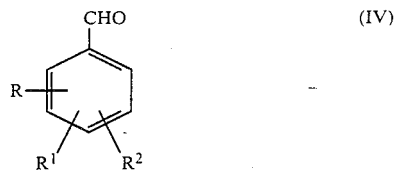
(IV)

wherein R, $R^1$ and $R^2$ are as defined in connection with formula II, if necessary (e.g. when M is an alkali metal) followed by treatment with a proton source, e.g. dilute acid.

When M is hydrogen the reaction may be carried out at room temperature or below in a suitable solvent, e.g. acetic acid and/or in the presence of a Lewis acid e.g. zinc chloride. If the aldehyde of formula IV and the tetrahydroquinoline of formula III (wherein M is H) are reacted simultaneously under dehydrating conditions then it is possible to produce the compounds of formula I directly without isolation of an intermediate hydroxy compound of formula II wherein X is H and Y is OH. Examples of suitable conditions for effecting such a reaction are the presence of a dehydrating agent such as an organic acid anhydride (including mixed anhydrides) e.g. acetic anhydride preferably at elevated temperature. Polyphosphoric acid or the like may also be used as the dehydrating agent. Hydroxy substituent groups may be protected in similar manner to that described in connection with the dehydration of compounds of formula II described above.

Accordingly this invention also provides a process for preparing a compound of formula I as hereinbefore defined which comprises reacting a compound of formula III wherein M is hydrogen with an aldehyde of formula IV as hereinbefore defined under dehydrating conditions, and if required removing one or more hydroxy protecting groups.

Compounds of formula II wherein X is OH and Y is hydrogen may be prepared by reacting a compound of formula

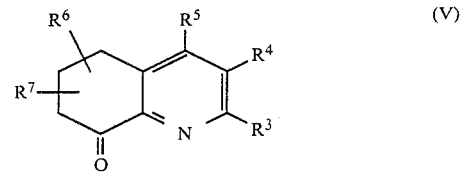
(V)

wherein $R^3$, $R^4$, $R^5$, $R^6$ and $R^7$ are as hereinbefore defined with a compound of formula

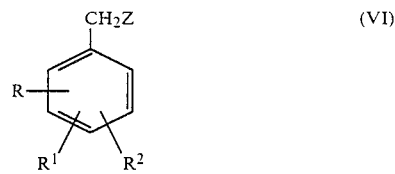
(VI)

wherein R, $R^1$ and $R^2$ are as hereinbefore defined in connection with formula II and Z is an alkali metal or MgHal where Hal is chlorine, bromine or iodine, followed by treatment with a proton source, e.g. dilute acid.

A further process for preparing compounds of formula I employs the Peterson reaction (J. Organic Chem.

TABLE 1-continued

| Compound No. | Structural formula | Physico-chemical property |
|---|---|---|
| 7 | Cl-C6H4-C(=O)-N(COCH2Cl)-N=C(CH3)2 | m.p. 49~51° C. |
| 8 | Cl-C6H4-C(=O)-N(CO-C6H5)-N=C(CH3)2 | m.p. 73~76° C. |
| 9 | Cl-C6H4-C(=O)-N(COOCH3)-N=C(CH3)2 | m.p. 95~97° C. |
| 10 | Cl-C6H4-C(=O)-N(CONHCH3)-N=C(CH3)2 | m.p. 119~123° C. |
| 11 | Cl-C6H4-C(=O)-N(COCH3)-N=C(CH3)(H) | m.p. 78~80° C. |
| 12 | Cl-C6H4-C(=O)-N(COCH3)-N=C(CH3)(C2H5) | m.p. 53~55° C. |
| 13 | Cl-C6H4-C(=O)-N(COCH3)-N=C(CH3)(C4H9-iso) | $n_D^{25}$ 1.5548 |
| 14 | Cl-C6H4-C(=O)-N(COCH3)-N=C(C3H7-n)(C3H7-n) | $n_D^{25}$ 1.5469 |
| 15 | Cl-C6H4-C(=O)-N(COCH3)-N=cyclohexyl(H) | m.p. 50~53° C. |
| 16 | Cl-C6H4-C(=O)-N(CH3)-N=C(H)(C6H5) | m.p. 148~150° C. |
| 17 | Cl-C6H4-C(=O)-N(COCH3)-N=C(H)(C6H5) | m.p. 83~85° C. |
| 18 | Cl-C6H4-C(=O)-N(CO-C6H5)-N=C(H)(C6H5) | m.p. 128~129° C. |
| 19 | Cl-C6H4-C(=O)-N(COCH3)-N=C(CH3)(C6H5) | m.p. 65~67° C. |
| 20 | 2-Cl-C6H4-C(=O)-N(COCH3)-N=C(CH3)2 | m.p. 30~33° C. |
| 21 | 3-Cl-C6H4-C(=O)-N(COCH3)-N=C(CH3)2 | $n_D^{25}$ 1.5721 |
| 22 | 2,4-Cl2-C6H3-C(=O)-N(COCH3)-N=C(CH3)2 | m.p. 142~143° C. |
| 23 | Br-C6H4-C(=O)-N(COCH3)-N=C(CH3)2 | m.p. 88~90° C. |
| 24 | Br-C6H4-C(=O)-N(COOCH3)-N=C(CH3)2 | m.p. 103~104° C. |
| 25 | F-C6H4-C(=O)-N(COCH3)-N=C(CH3)2 | $n_D^{25}$ 1.5458 |
| 26 | 2-CF3-C6H4-C(=O)-N(COCH3)-N=C(CH3)2 | $n_D^{25}$ 1.5050 |
| 27 | CH3-C6H4-C(=O)-N(COCH3)-N=C(CH3)2 | m.p. 69~71° C. |
| 28 | CH3O-C6H4-C(=O)-N(COCH3)-N=C(CH3)2 | m.p. 78~81° C. |

In order to use the compounds according to the invention as insecticides, the compounds may be used as they are or may be diluted with a suitable carrier such as water or a solid powder, to which an adjuvant is added. If necessary, adjuvants such as a wetting agent, a spreader, a dispersing agent, an emulsifier, a binder and the like may be added to the mixture for use as various types of preparations such as wettable powders, solutions, emulsions, sols (flowable), dusts, DL(driftless)-type dusts, granules, and fine granules.

In preparing these chemicals, there are used as a liquid carrier water, aromatic hydrocarbons, aliphatic hydrocarbons, alcohols, esters, ketones, acid amides, and highly polar solvents such as dimethylformamide, dimethylsulfoxide and the like; as a solid carrier mineral powders such as clay, talc, kaolin, bentonite, diatomaceous earth, calcium carbonate, silicic acid and the like, and organic powders such as wood meal; and as an adjuvant nonionic, anionic, cationic and amphoteric surface active agents, ligninsulfonic acid or its salts, gums, fatty acid salts, pastes such as of methyl cellulose, and the like.

The preparations such as wettable powders, solutions and emulsions may contain the active ingredient(s) in the amount of 1–95% by weight, usually 2–75% by weight. These preparations are diluted with water to a concentration of 0.0001–10% by weight. Dusts and granules usually contain 0.1–10% by weight of the active ingredient(s). The liquid concentrates such as emulsions and sols (flowable agent) can be used as they are, without dilution.

In using the compound of the invention for insecticidal purposes, it is possible to broaden its applicability by mixing with other insecticides, fungicides, herbicides and plant growth regulators, and is also possible to realize synergistic effects as the case may be. The insecticidial effect of the compound of the invention can be greatly improved by the addition of a synergist such as propenyl butoxide (P.B.), octachlorodipropylether, N-octyl bicycloheptene dicarboximide.

The present invention will be particularly described by way of examples, which should not be construed as limiting the invention thereto. The parts as given in examples are parts by weight.

EXAMPLE 4

Emulsion 20 parts of the compound No. 1, 30 parts of dimethyl formamide, 35 parts of xylene and 15 parts of polyoxyethylene alkylarylether were mixed uniformly to obtain an emulsion containing 20% of the active ingredient.

EXAMPLE 5

Wettable powder 20 parts of the compound No. 2, 5 parts of polyoxyethylene alkylarylether, 3 parts of calcium lignin sulfonate and 72 parts of diatomaceous earth were mixed uniformly to obtain a wettable powder containing 20% of the active ingredient.

EXAMPLE 6

Dust 3 parts of the compound No. 10, 0.5 part of anhydrous silicic acid, 50 parts of clay and 46.5 parts of talc were mixed uniformly to obtain a dust containing 3% of the active ingredient.

The following experiments are to explain the usefulness of the insecticides which contain the active ingredients according to the present invention.

Experiment 1

(Test for controlling *Culex pipiens pallens*)

250 ml of a test liquid of the determined concentration of an emulsion prepared according to the Example 4 was placed in a Petri dish of 9 cm in diameter and 6 cm in height, in which 20 4th-instar-larvae were set free. After allowing stand for 24 hours under the constant temperature of 25° C., the mortality (%) was determined. This experiment was performed three times and the average mortality was calculated. The results were tabulated in Table 2.

TABLE 2

| Compound No. | Effective ingredient concentration (ppm) | Mortality (%) |
| --- | --- | --- |
| 1 | 1 | 100 |
| 2 | " | 100 |
| 3 | " | 100 |
| 4 | " | 100 |
| 5 | " | 100 |
| 6 | " | 100 |
| 7 | " | 100 |
| 8 | " | 100 |
| 9 | " | 100 |
| 10 | " | 100 |
| 11 | " | 100 |
| 12 | " | 100 |
| 13 | " | 100 |
| 14 | " | 100 |
| 15 | " | 100 |
| 16 | " | 100 |
| 17 | " | 100 |
| 18 | " | 100 |
| 19 | " | 100 |
| 20 | " | 100 |
| 21 | " | 100 |
| 22 | " | 100 |
| 23 | " | 100 |
| 24 | " | 100 |
| 25 | " | 100 |
| 26 | " | 100 |
| 27 | " | 100 |
| 28 | " | 100 |
| Comparative chemical A | " | 58 |
| Comparative chemical B | " | 44 |
| Comparative chemical C | " | 46 |
| Comparative chemcial D | " | 44 |
| Comparative chemical E | " | 95 |
| Non-treated plot | — | 0 |

In the foregoing table, the comparative chemicals A-D are the compounds described in "J. Pharm. Soc., Japan 79, 103–104 (1959) and, in chemical names, "A" is 1,1-dibenzoyl-2-isopropylidene hydrazine, "B" is 1-benzoyl-1-p-nitrobenzoyl-2-isopropylidene hydrazine, "C" is 1-benzoyl-1-acetyl-2-isopropylidene hydrazine and "D" is 1-benzoyl-1-phenyl-2-isopropylidene hydrazine. "E" is a fungicidal preparation containing O,O-dimethyl-O-(3-methyl-4-nitrophenyl)phosphorothioate, available from the market under the common name of MEP.

Experiment 2

(Test for effect of controlling *Muska domestica*)

A filter paper was placed on the bottom of a glass Petri-dish having a diameter of 9 cm, to which 1 ml of a test liquid of the determined concentration of an emulsion prepared according to Example 4 was dropped. In this Petri-dish 10 house flies of the Takatsuki strain (Organo-phosphorus-susceptible strain) or of the 3rd Yumenoshima strain (multi-resistant strain) were set free. After allowing to stand for 48 hours under a constant temperature of 25° C., the number of knock down insects was determined to obtain the mortality (%). This experiment was performed three times for one concentration. Average mortality was calculated and the results were tabulated in Table 3.

TABLE 3

| Compound No. | Mortality (%) | | | |
|---|---|---|---|---|
| | House fly (Takatsuki strain) Effective ingredient concentration (ppm) | | House fly (The third Yumenoshima strain) Effective ingredient concentration (ppm) | |
| | 300 | 100 | 300 | 100 |
| 1 | 100 | 87 | 100 | 83 |
| 2 | 100 | 100 | 100 | 100 |
| 3 | 100 | 93 | 100 | 93 |
| 4 | 100 | 90 | 100 | 93 |
| 5 | 100 | 100 | 100 | 97 |
| 6 | 100 | 87 | 100 | 80 |
| 7 | 100 | 90 | 100 | 90 |
| 8 | 100 | 93 | 100 | 93 |
| 9 | 100 | 100 | 100 | 93 |
| 10 | 100 | 87 | 100 | 90 |
| 11 | 100 | 100 | 100 | 100 |
| 12 | 100 | 100 | 100 | 100 |
| 13 | 100 | 97 | 100 | 93 |
| 14 | 100 | 90 | 100 | 93 |
| 15 | 100 | 87 | 100 | 83 |
| 16 | 100 | 90 | 100 | 90 |
| 17 | 100 | 90 | 100 | 81 |
| 18 | 100 | 90 | 100 | 83 |
| 19 | 100 | 93 | 100 | 90 |
| 20 | 100 | 93 | 100 | 90 |
| 21 | 100 | 100 | 100 | 97 |
| 22 | 100 | 93 | 100 | 87 |
| 23 | 100 | 97 | 100 | 90 |
| 24 | 100 | 90 | 100 | 90 |
| 25 | 100 | 100 | 100 | 100 |
| 26 | 100 | 100 | 100 | 97 |
| 27 | 100 | 87 | 100 | 83 |
| 28 | 100 | 87 | 100 | 80 |
| Comparative chemical A | 83 | 50 | 80 | 45 |
| Comparative chemical B | 80 | 55 | 83 | 45 |
| Comparative chemical C | 87 | 55 | 90 | 50 |
| Comparative chemical D | 80 | 50 | 80 | 45 |
| Comparative chemical E | 100 | 90 | 0 | 0 |
| Comparative chemical F | 100 | 100 | 0 | 0 |
| Non-treated plot | 0 | 0 | 0 | 0 |

In the foregoing table, the comparative chemicals A-E are the same compounds as explained hereinbefore, and the comparative chemical F is an insecticide containing 0,0-dimethyl S-(1,2-dicarbethoxyethyl)phosphorothiolo-thioate (Malathon).

Experiment 3

(Test for controlling *Hylemya platura*)

A 60 cm-wideditch in a test field was incorporated with fish dregs and then allowed to stand for 22 days, so that egg-laying of *Hylemya platura* was induced. The fish dregs were covered with soil, and the soil was mixed with a test agent of the determined amount of the emulsion prepared according to Example 4. The soil thus treated was sown with kindey beans (New Edogawa species) and covered with soil. On the 20th day after the treatment, the number of germination and the degree of injury were examined to obtain the control value (%) from the injury index described hereinbelow. The results were tabulated in Table 4.

| | Index | Degree |
|---|---|---|
| None | 0 | No damage |
| Small | 1 | Slightly damaged; no effect on subsequent growth |
| Light | 3 | Damaged; however no effect on subsequent growth |
| Middle | 5 | Comparatively damaged and somewhat bad effect on growth; however, recovery is possible |
| Much | 8 | Damaged considerably and very poor in growth; recovery is impossible |
| | 10 | Heavily damaged; impossible in germination or died after germination |

$$\text{Injury index} = \frac{\Sigma(\text{Index for each injury degree}) \times (\text{Number of strains for each injury degree})}{\text{Number of strains examined} \times \text{Maximum of index}} \times 100$$

Control value (%) = 100 − Injury index

TABLE 4

| Compound No. | Amount of effective ingredient (g/10 are) | Germination rate (%) | Control value (%) |
|---|---|---|---|
| 2 | 150 | 100 | 100 |
| 3 | " | 98 | 100 |
| 9 | " | 98 | 100 |
| 10 | " | 100 | 100 |
| 20 | " | 100 | 100 |
| 22 | " | 96 | 100 |
| 23 | " | 92 | 100 |
| 25 | " | 100 | 100 |
| Comparative chemical A | " | 94 | 60 |
| Comparative chemical B | " | 92 | 56 |
| Comparative chemical C | " | 98 | 62 |
| Comparative chemical D | " | 94 | 56 |
| Comparative chemical G | " | 100 | 94 |
| Non-treated plot | — | 100 | 0 |

In the foregoing table, comparative chemicals A-D are the same as those described hereinbefore, and "G" is an insecticide containing 0,0-diethyl-0-(2,4-dichlorophenyl)phosphorothionate (ECP).

What we claim is:

1. A benzoyl hydrazone derivative of the general formula

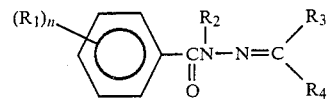

wherein $R_1$ is a lower alkyl group, a lower alkoxy group, a halogen atom or trifluoromethyl; n is 1 or 2; $R_2$ is a lower alkyl group, an alkylcarbonyl group, a halogenated lower alkylcarbonyl group, a benzoyl group, a lower alkoxycarbonyl group or a lower alkylcarbamoyl group; and $R_3$ and $R_4$ individually represent hydrogen atom, a lower alkyl group or a phenyl group, or $R_3$ and $R_4$ together can form a cyclohexane ring.

2. An insecticide composition which comprises as an active ingredient an effective insecticidal amount of a benzoyl hydrazone derivative of the formula

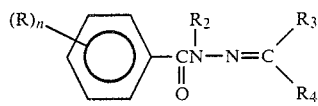

wherein $R_1$ is a lower alkyl group, a lower alkoxy group, a halogen atom or trifluoromethyl; n is 1 or 2; $R_2$ is a lower alkyl group, an alkylcarbonyl group, a halogenated lower alkylcarbonyl group, a benzoyl group, a lower alkoxycarbonyl group or a lower alkylcarbamoyl group; and $R_3$ and $R_4$ individually represent hydrogen atom, a lower alkyl group or a phenyl group, or $R_3$ and $R_4$ together can form a cyclohexane ring, in a suitable carrier.

* * * * *